United States Patent
Wang et al.

(10) Patent No.: US 8,837,803 B2
(45) Date of Patent: Sep. 16, 2014

(54) METHOD AND APPARATUS FOR DETERMINING MEAN CELL VOLUME OF RED BLOOD CELLS

(75) Inventors: Zhizhou Wang, Princeton, NJ (US); Min Xie, Plainsboro, NJ (US); Anil Patil, Iselin, NJ (US); Chong Chen, Irvine, CA (US); Shaohong Wang, Belle Mead, NJ (US); Cord Mueller, Middletown, CT (US)

(73) Assignee: Abbott Point of Care, Inc., Princeton, NJ (US)

( * ) Notice: Subject to any disclaimer, the term of this patent is extended or adjusted under 35 U.S.C. 154(b) by 183 days.

(21) Appl. No.: 12/982,422

(22) Filed: Dec. 30, 2010

(65) Prior Publication Data

US 2011/0164803 A1 Jul. 7, 2011

Related U.S. Application Data (60) Provisional application No. 61/291,441, filed on Dec. 31, 2009.

(51) Int. Cl.
*G06K 9/00* (2006.01)
*G01N 33/49* (2006.01)

(52) U.S. Cl.
CPC ............................. *G01N 33/49* (2013.01)
USPC ........................ 382/134; 382/128; 382/133

(58) Field of Classification Search
USPC ............................ 382/134, 133, 128
See application file for complete search history.

(56) References Cited

U.S. PATENT DOCUMENTS

| | | | |
|---|---|---|---|
| 4,023,716 A | 5/1977 | Shapiro | |
| 4,197,088 A | 4/1980 | Meserol et al. | |
| 4,487,081 A | 12/1984 | DeVaughn et al. | |
| 4,615,878 A | 10/1986 | Kass | |
| 5,012,818 A | 5/1991 | Joishy | |

(Continued)

FOREIGN PATENT DOCUMENTS

| | | |
|---|---|---|
| DE | 10011235 | 9/2001 |
| DE | 10240742 | 3/2004 |

(Continued)

OTHER PUBLICATIONS

Wan et al. -"Contact Mechanics of a Thin-Walled Capsule adhered onto a Rigid planar Substrate" Medical & Biological Engineering & Computing 2001, vol. 39, p. 605-608.*

(Continued)

*Primary Examiner* — Matthew Bella
*Assistant Examiner* — Weiwen Yang
(74) *Attorney, Agent, or Firm* — O'Shea Getz P.C.

(57) ABSTRACT

A method and apparatus for determining a cell volume of a red blood cell is provided. The method includes the steps of: a) depositing a sample into an analysis chamber, the chamber defined by an first panel interior surface, a second panel interior surface, and a known or determinable height, which height is such that at least one red blood cell subject to a sphering agent assumes a partially compressed spherical shape in contact with the interior surfaces; b) imaging the at least one partially compressed spherical red blood cell contacting the interior surfaces, and producing image signals; c) determining a radius of the partially compressed spherical red blood cell from the image signals; and d) determining a volume of the imaged red blood cell using the determined radius.

13 Claims, 3 Drawing Sheets

(56) References Cited

U.S. PATENT DOCUMENTS

| | | |
|---|---|---|
| 5,068,181 A | 11/1991 | Driscoll |
| 5,192,511 A | 3/1993 | Roach |
| 5,284,771 A | 2/1994 | Fan et al. |
| 5,447,838 A | 9/1995 | Meiklejohn et al. |
| 5,454,268 A | 10/1995 | Kim |
| 5,460,782 A | 10/1995 | Coleman et al. |
| 5,739,042 A | 4/1998 | Frengen |
| 5,768,407 A | 6/1998 | Shen et al. |
| 5,770,160 A | 6/1998 | Smith et al. |
| 5,851,835 A * | 12/1998 | Groner .......................... 436/63 |
| 5,948,686 A | 9/1999 | Wardlaw |
| 6,127,184 A | 10/2000 | Wardlaw |
| 6,235,536 B1 | 5/2001 | Wardlaw |
| 6,544,793 B2 | 4/2003 | Berndt |
| 6,723,290 B1 | 4/2004 | Wardlaw |
| 6,730,521 B1 | 5/2004 | Cassells |
| 6,819,408 B1 | 11/2004 | Scrivens |
| 6,866,823 B2 | 3/2005 | Wardlaw |
| 6,929,953 B1 | 8/2005 | Wardlaw |
| 7,731,901 B2 | 6/2010 | Wardlaw |
| 7,850,916 B2 | 12/2010 | Wardlaw |
| 7,903,241 B2 | 3/2011 | Wardlaw et al. |
| 7,912,534 B2 | 3/2011 | Grinvald |
| 7,929,121 B2 | 4/2011 | Wardlaw |
| 7,929,122 B2 | 4/2011 | Wardlaw |
| 7,951,599 B2 | 5/2011 | Levine |
| 8,081,303 B2 | 12/2011 | Levine |
| 8,133,738 B2 | 3/2012 | Levine |
| 8,310,658 B2 | 11/2012 | Wardlaw |
| 8,361,799 B2 | 1/2013 | Levine |
| 2002/0028158 A1 | 3/2002 | Wardlaw |
| 2002/0131902 A1 | 9/2002 | Levy |
| 2003/0025896 A1 | 2/2003 | Oever et al. |
| 2003/0224534 A1 | 12/2003 | Kawate |
| 2004/0048330 A1 | 3/2004 | Bittner |
| 2004/0165090 A1 | 8/2004 | Ning |
| 2005/0002826 A1 | 1/2005 | Oguni et al. |
| 2005/0026197 A1 | 2/2005 | Dertinger |
| 2005/0277159 A1 | 12/2005 | Lehmann et al. |
| 2006/0159962 A1 | 7/2006 | Chandler et al. |
| 2006/0258018 A1 | 11/2006 | Curl et al. |
| 2007/0087442 A1 | 4/2007 | Wardlaw |
| 2007/0243117 A1 | 10/2007 | Wardlaw |
| 2008/0070317 A1 | 3/2008 | Bradshaw et al. |
| 2009/0238438 A1 | 9/2009 | Wardlaw |
| 2010/0015691 A1 | 1/2010 | Krogh |

FOREIGN PATENT DOCUMENTS

| | | |
|---|---|---|
| EP | 0366151 | 5/1990 |
| EP | 0642829 | 3/1995 |
| EP | 1239284 | 9/2002 |
| GB | 2254414 | 10/1992 |
| JP | 6308119 | 11/1994 |
| WO | 9802727 | 1/1998 |
| WO | 0057891 | 5/2000 |
| WO | 0223154 | 3/2002 |

OTHER PUBLICATIONS

Pfeifer -"Solder Bump Size and Shape Modeling and Experimental Validation" IEEE, 1997, 452-457.*

Sun et al, "Microminiaturized immunoassays using quantum dots as fluorescent label by laser confocal scanning fluorescence detection," Journal of Immunological Methods, Elsevier Science Publishers, vol. 249, No. 1-2, pp. 85-89, Mar. 2001.

Goldman et al., "Multiplexed Toxin Analysis using Four Colors of Quantum Dot Fluororeagents," Analytical Chemistry, American Chemical Society, vol. 76, No. 3, pp. 684-688, Feb. 2004.

Matzdorff et al., "Quantitative assessment of platelets, platelet microparticles, and platelet aggregates in flow cytometry, "The Journal of Laboratory and Clinical Medicine, vol. 131, No. 6, pp. 507-517, Jun. 1998.

Hu Hu et al, "Effects of insulin on platelet and leukocyte activity in whole blood," Thrombosis Research, vol. 107, No. 5, pp. 209-215, Sep. 2002.

Sbrana et al., "Relationships between optical aggregometry (type born) and flow cytometry in evaluating ADP-induced platelet activation," Cytometry, Part B, Clinical Cytometry, vol. 74, No. 1, pp. 30-39, Jan. 2008.

Fishbane et al., "Reticulocyte hemoglobin content in the evaluation of iron status of hemodialysis patients", Kidney International, vol. 52, pp. 217-222, 1997.

Wray et al. "Characterization of the Near Infrared Absorption Spectra of Cytochrome aa3 and Haemoglobin for the Non-Invasive Monitoring of Cerebral Oxygenation", Biochimica et Ciophysica Acta, 933 (1988), 184-192.

Kim et al. "Engineering in Medicine and Biology: Extinction Coefficients of Hemoglobin for Near-Infrared Spectroscopy of Tissue", Mar./Apr. 2005.

Hematocrit/HCT and Caluated Hemoglobin/HB, Article 714178-00H, Rev. Date: Jun. 11, 2008.

Wood et al., "Resonance Raman Spectroscopy of Red Blood Cells Using Near-Infrared Laser Excitation", Analytical and Bioanalytical Chemistry, vol. 387, No. 5, Dec. 7, 2006, pp. 1691-1703.

Ellis et al., "Applicaton of Image Analysis for Evaluation of Red Blood Cell Dynamics in Capillaries", Microvascular Research, vol. 44, No. 2, Sep. 1, 1992, pp. 214-225.

* cited by examiner

METHOD AND APPARATUS FOR DETERMINING MEAN CELL VOLUME OF RED BLOOD CELLS

The present application is entitled to the benefit of and incorporates by reference essential subject matter disclosed in U.S. Provisional Patent Application Ser. No. 61/291,441, filed Dec. 31, 2009.

BACKGROUND OF THE INVENTION

1. Technical Field

The present invention relates to apparatus and methods for analysis of blood samples in general, and for the determination of the cell volume and mean cell volume of red blood cells within a sample in particular.

2. Background Information

Physicians, veterinarians and scientists have examined human and animals' biologic fluids, especially blood, in order to determine constituent particulate quantities as well as to identify the presence of unusual particulates not seen in healthy subjects. The particulates generally measured, quantified and identified include red blood cells (RBCs), white blood cells (WBCs), and platelets. RBC analyses can include determinations of RBC number, size, volume, shape, hemoglobin content and concentration, and the hematocrit (also referred to as the packed cell volume).

Known blood examination techniques, described in detail medical texts such as Wintrobe's Clinical Hematology 12th Edition, generally divide the examination methods into manual, centrifugal, and impedance type methods. Manual methods for cell enumeration typically involve the creation of an accurately determined volume of a blood or fluid sample that is quantitatively diluted and visually counted in a counting chamber. Manual examination methods include examining a peripheral smear where the relative amounts of the particulate types are determined by visual inspection. Centrifugal examination methods involve centrifuging the sample, causing the sample to separate into constituent layers according to the relative densities of the constituents. Impedance methods involve the examination of an accurate volume of blood which is treated according to the particulate being measured; e.g., lysing RBCs for enumeration of the nucleated cells and volumetrically diluting the sample in a conductive fluid. The process typically involves monitoring a current or voltage applied to sample passing through a narrow passage to determine the effect particles have on the current/voltage as the particles pass through in single file.

All of the aforementioned methods, other than the peripheral smear or centrifugal separation, require dispensing a precise volume of sample. Inaccuracies in the sample volume will result in quantitative errors of the same magnitude in the associated analysis. With the exception of centrifugal methods, all of the aforementioned methods also require the sample to be mixed with one or more liquid reagents or diluents, and also require calibration of the instrument to obtain accurate results. In the case of peripheral smears, a high degree of training is needed to properly examine the smear. A number of the aforementioned methods generate large volumes of contaminated waste which is expensive to handle.

SUMMARY OF THE INVENTION

According to an aspect of the present invention, a method for determining a cell volume of a red blood cell within a blood sample is provided. The method includes the steps of: a) depositing the sample into an analysis chamber adapted to quiescently hold the sample for analysis, the chamber defined by an interior surface of a first panel and an interior surface of a second panel, wherein both panels are transparent, and the chamber has a known or determinable height extending between the interior surfaces of the panels, which height is such that at least one red blood cell subject to an isovolumetric sphering agent assumes a partially compressed spherical shape in contact with the interior surfaces; b) imaging the at least one partially compressed spherical red blood cell contacting the interior surfaces, and producing image signals; c) determining a radius of the partially compressed spherical red blood cell contacting the interior surfaces from the image signals; and d) determining a volume of the imaged red blood cell using the determined radius.

According to another aspect of the present invention, a method for determining a mean cell volume of red blood cells within a blood sample is provided. The method includes the steps of: a) depositing the sample into an analysis chamber adapted to quiescently hold the sample for analysis, the chamber defined by an interior surface of a first panel and an interior surface of a second panel, wherein both panels are transparent, and the chamber has a known or determinable height extending between the interior surfaces of the panels, which height is such that at least one red blood cell subject to an isovolumetric sphering agent assumes a partially compressed spherical shape in contact with the interior surfaces; b) imaging a plurality of partially compressed spherical red blood cells within the sample, which red blood cells are contacting the interior surfaces, and producing image signals reflecting the optical density of the red blood cells contacting the interior surfaces; c) determining a threshold density value for a predetermined area surrounding each of a number of the imaged red blood cells, and selecting at least some of the imaged red bloods cells having substantially similar threshold density values; d) determining a radius of each of the selected red blood cells having substantially similar threshold density values from the image signals; e) determining a volume of each of the selected red blood cells using its respective determined radius; and f) determining a mean red blood cell volume using the determined volumes of the selected red blood cells.

According to another aspect of the present invention, an apparatus for determining a cell volume of at least one red blood cell within a substantially undiluted blood sample is provided. The apparatus includes an analysis chamber, an imaging unit, and a programmable analyzer. The analysis chamber is adapted to quiescently hold the sample for analysis. The chamber is defined by an interior surface of a first panel, and an interior surface of a second panel. Both panels are transparent. The chamber has a known or determinable height extending between the interior surfaces of the panels. The height is such that at least one red blood cell within the sample will assume a partially compressed spherical shape. The imaging unit includes an illuminator and an image dissector. The unit is operable to image the at least one red blood cell contacting the interior surfaces, and produce image signals representative of such imaged red blood cell. The programmable analyzer is adapted to determine, using the image signals, a radius of the partially compressed spherical red blood cell contacting the interior surfaces from the image signals. The analyzer is further adapted to determine a volume of the imaged red blood cell using the determined radius.

The present method and apparatus, and advantages associated therewith, will become more readily apparent in view of the detailed description provided below, including the accompanying drawings.

DETAILED DESCRIPTION OF EMBODIMENTS OF THE INVENTION

The present method and apparatus for analyzing a sample of substantially undiluted whole blood allows the determination of a volume of a red blood cell (RBC) within the sample, and the determination of the mean cell volume (MCV) within the sample, without the addition of any diluents, dyes or reagents, other than one or more anticoagulants and one or more isovolumetric sphering agents.

The present method utilizes an analysis chamber that is operable to quiescently hold a sample of substantially undiluted anticoagulated whole blood for analysis. The chamber is typically sized to hold about 0.2 to 1.0 µl of sample, but the chamber is not limited to any particular volume capacity. The phrase "substantially undiluted" as used herein describes a blood sample which is either not diluted at all or has not been diluted purposefully, but includes some reagents added for purposes of the analysis. If the addition of the reagent dilutes the sample at all, such dilution has no clinically significant impact on the analysis performed. Typically, the only reagents used in performing the present method are anticoagulants (e.g., EDTA, heparin) and an isovolumetric sphering agent (e.g., a zwitterionic detergent or similarly functioning reagent). These reagents are generally added in dried form. Under certain circumstances (e.g., very rapid analysis), it may not be necessary to add the anticoagulating agent, but it is preferable to do so in most cases to ensure the sample is in a form acceptable for analysis. The term "quiescent" describes that when the sample is deposited within the chamber for analysis, the sample is not purposefully moved relative to the chamber during the analysis; i.e., the sample resides quiescently within the chamber. To the extent that motion is present within the blood sample, it will predominantly be due to Brownian motion of the formed constituents within the sample, which motion is not disabling of the use of the device of this invention.

Figure 1:
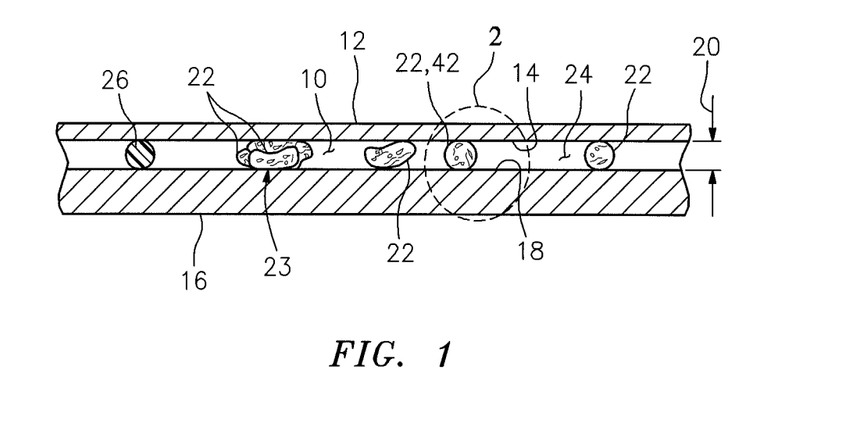
FIG. 1 is a cross-sectional diagrammatic representation of an analysis chamber.
Figure 2:
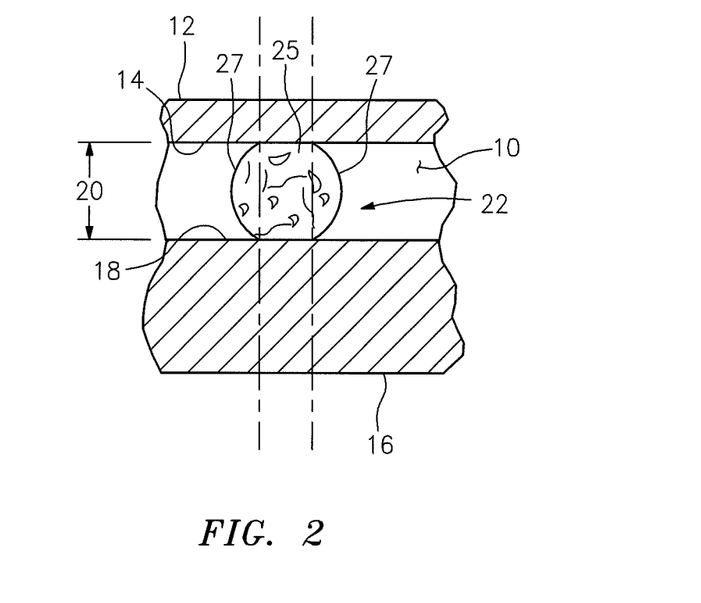
FIG. 2 is an enlarged view of a portion of the analysis chamber shown in FIG. 1.

Now referring to FIGS. 1-2, the analysis chamber 10 is defined by a first panel 12 having an interior surface 14, and a second panel 16 having an interior surface 18. The panels 12, 16 are both sufficiently transparent to allow the transmission of light along predetermined wavelengths there through in an amount sufficient to perform the optical density analysis described below. At least a portion of the panels 12, 16 are parallel with one another, and within that portion the interior surfaces 14, 18 are separated from one another by a height 20 such that at least some individual RBCs 22 within a sample each individually contact both interior surfaces 14, 18, and one or more RBC void areas (e.g., lacunae) 24 within the quiescent sample extend between the interior surfaces. The present method can utilize a variety of different analysis chambers types having the aforesaid characteristics, and is not therefore limited to any particular type of analysis chamber. An analysis chamber having parallel panels 12, 16 simplifies the analysis and is therefore preferred, but is not required for the present invention; e.g., a chamber having one panel disposed at a known non-parallel angle relative to the other panel could be used. In preferred embodiments, the chamber includes at least three separators 26 disposed between the panels 12, 16. The separators 26 can be any structure that is disposable between the panels 12, 16, operable to space the panels 12, 16 apart from one another. The dimension of a separator 26 that extends between the panels 12, 16 is referred to herein as the height of the separator 26. The heights of the separators 26 typically do not equal one another exactly (e.g., manufacturing tolerances), but are within commercially acceptable tolerance for spacing means used in similar analysis apparatus. Spherical beads are an example of an acceptable separator 26, and a specific example of an acceptable spherical bead is a polystyrene bead that is commercially available, for example, from Thermo Scientific of Fremont, Calif., U.S.A., catalogue no. 4204A, in four micron (4 µm) diameter. An acceptable analysis chamber is described in greater detail in U.S. Patent Application Publication Nos. 2007/0243117, 2007/0087442, and U.S. Provisional Patent Application Nos. 61/165,750, filed Apr. 1, 2009; and 61/287,955 filed Dec. 18, 2009, all of which are hereby incorporated by reference in their entirety.

An acceptable chamber height is defined as one in which at least some of the RBCs within the sample individually contact both interior surfaces of the chamber panels. A chamber height of about two to six microns (2-6 µm) is acceptable for individual RBCs for most animal species based on typical RBC sizes and the fact that RBCs can be deformed to some degree (e.g., the partially compressed sphere discussed above).

An isovolumetric sphering agent (e.g., a zwitterionic detergent or similarly functioning reagent) is admixed with at least a portion of the sample to cause at least some of the RBCs to assume a substantially spherical geometry. RBCs 22 in their natural form are often bioconcave disc shaped rather than spherically shaped. As a result, absent the effect of the isovolumetric sphering agent, a large percentage of the disc shaped RBCs 22 will not contact both of the chamber panels 12, 16. Increasing the number of RBCs 22 that have a substantially spherical geometry will increase the number of RBCs 22 in contact with both panels 12, 16, including some cells 42 that are restrained by the chamber panels, but would otherwise be spherical. The term "spherical" as used herein refers to the geometry of a RBC that has been subjected to an adequate amount of isovolumetric sphering agent. As the noun implies, the "isovolumetric" sphering agent causes the RBC to extend outwardly in all directions, thereby assuming a substantially spherical shape. In some instances, the RBC structure will not allow the RBC to assume a perfectly spherical shape when subjected to the agent. For purposes of describing the present invention, the term "spherical" as used herein includes those shapes that are perfectly spherical and also those shapes that are substantially spherical as a result of the sphering agent.

Figure 3:
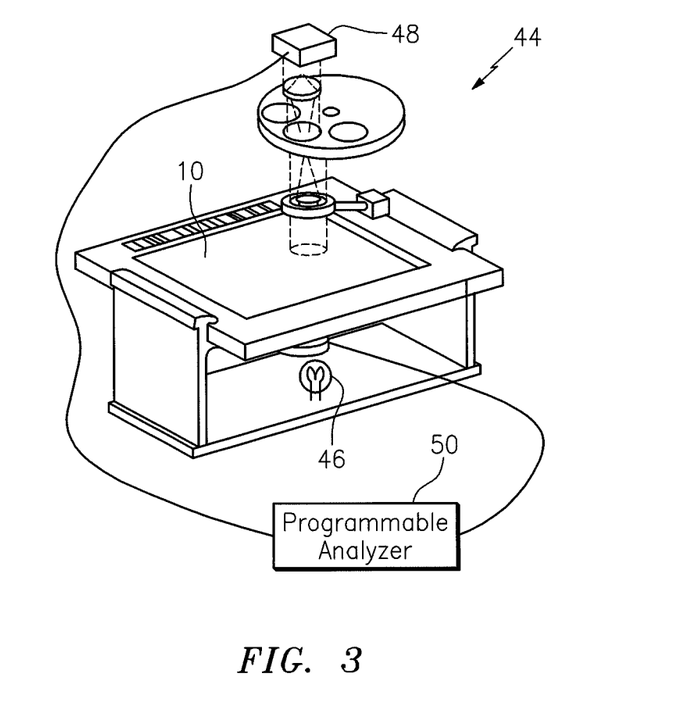
FIG. 3 is a diagrammatic schematic of an analysis device that may be used with the present method.

Referring to FIG. 3, the analysis of the sample quiescently disposed within the chamber 10 is performed using an analysis device 44 that is operable to image at least a portion of the sample and perform an analysis on the image. The image is produced in a manner that permits the optical density of sample to be determined on a per unit basis. The term "per unit basis" or "image unit" means a defined incremental unit into which the image of the sample can be dissected. A pixel which is generally defined as the smallest element of an image that can be individually processed within a particular imaging system is an example of an image unit, and an image unit may also include a small number of pixels in a collective unit. The magnification of an imaging device can also be described in linear terms (e.g., microns per pixel at the focal plane), where the linear dimension is along a particular axis of an orthogonal grid applied to the image. The actual area of the sample captured by pixels (or other image units) of the sensor at the focal plane is therefore a function of the magnification factor applied by the imaging device. Hence, the magnification of the imaging device should be known or determinable. The volume associated with a pixel is therefore the area of the image per pixel times the known chamber height, since the point in the chamber that was sensed is one where the RBC extends across the entire chamber. If the magnification was 0.5 microns per pixel, for example, an image occupying 200 pixels would have an area of 50 square microns, and a volume of 50 square microns times the chamber height. Optical density ("OD") is a measure of the amount of light absorbed relative to the amount of light transmitted through a medium; e.g., the higher the "OD" value, the greater the amount of light absorbed during transmission. OD can be quantitatively described in optical density units ("OD") or fractions thereof.

The analysis device 44 includes a sample illuminator 46, an image dissector 48, and a programmable analyzer 50. The sample illuminator 46 includes a light source that selectively produces light throughout a wavelength range broad enough to be useful for an RBC cell volume analysis (e.g., approximately 400-670 nm; light at about 413 nm and about 540 nm is particularly effective in determining the optical density of the RBCs), and typically includes optics for manipulating the light. The sample illuminator 46 utilizes transmittance to produce an image. The light transmission properties of the sample can be measured, for example, by positioning a light source on one side of the sample residing within the chamber 10, directing the light through the sample quiescently disposed between chamber panels, and thereafter capturing the light using the image dissector. An example of an acceptable image dissector 48 is a charge couple device (CCD) type image sensor that converts an image of the light passing through the sample into an electronic data format. Complementary metal oxide semiconductor ("CMOS") type image sensors are another example of an image sensor that can be used. The present invention is not limited to either of these examples, however. The programmable analyzer 50 includes a central processing unit (CPU) and is connected to the sample illuminator 46 and image dissector 48. The CPU is adapted (e.g., programmed) to selectively perform the functions necessary to perform the present method. It should be noted that the functionality of programmable analyzer 50 may be implemented using hardware, software, firmware, or a combination thereof. A person skilled in the art would be able to program the processing unit to perform the functionality described herein without undue experimentation. U.S. Pat. No. 6,866,823 entitled "Apparatus for Analyzing Biologic Fluids" and issued Aug. 15, 2005, which is hereby incorporated by reference in its entirety, discloses an analysis device that could be programmed to be used with the present invention.

The analysis device 44 is adapted to determine an OD value associated with the detected light signal, which OD value is determined on a per image unit basis for an imaged portion of the sample. The OD of a RBC 22 is determined by the hemoglobin concentration within the cell, the molar extinction coefficient (also referred to as molar absorptivity) for hemoglobin at a given wavelength, and the distance of the light path traveled through the hemoglobin and can be represented by the following relationship:

$$OD = \epsilon c L \quad \text{Eqn. 1}$$

where $\epsilon$=hemoglobin molar extinction coefficient, c=hemoglobin concentration, and L=distance traveled through the RBC 22 (i.e., the distance traveled through the hemoglobin disposed within the cell). The molar extinction coefficient is an intrinsic property of the hemoglobin that can be derived by experimentation, or through empirical data currently available. In analysis device embodiments that utilize light sources having an error margin (e.g., an LED having a design rated wavelength, plus or minus some amount), it is useful for accuracy purposes to initially calibrate the device and determine the hemoglobin molar extinction coefficient, which coefficient can then be used with that particular device until the light source is replaced, at which time the device can be recalibrated.

Figure 4A:
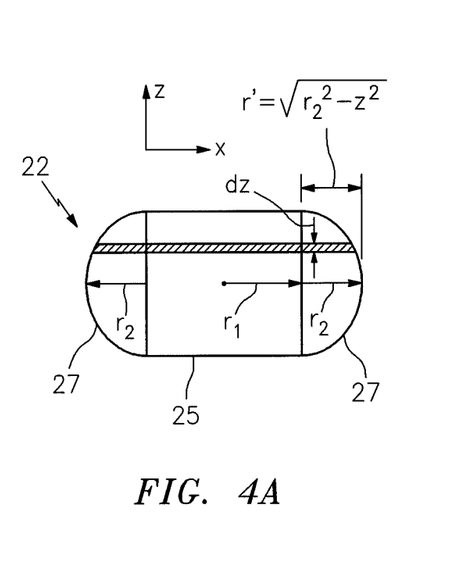
FIG. 4A is a geometric side representation of a RBC compressed within an analysis chamber.
Figure 4B:
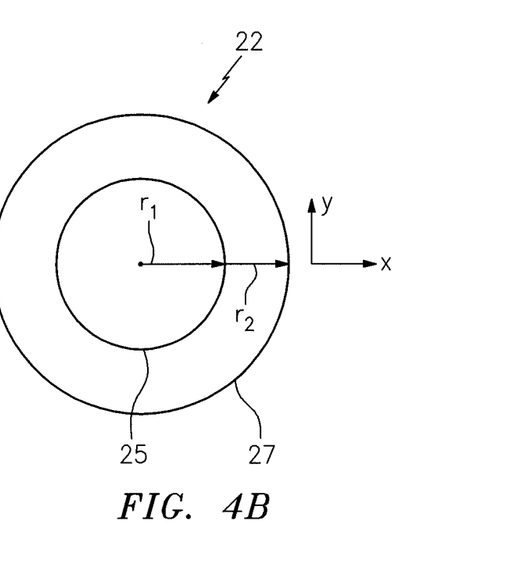
FIG. 4B is a geometric top representation of the RBC shown in FIG. 4A.

RBCs 22 that contact both interior surfaces of the chamber 10 have an OD profile similar to that of a partially compressed sphere (see FIGS. 2 and 4A-4B). A partially compressed sphere can be geometrically modeled as shown in FIG. 4A in the X-Z plane and FIG. 4B in the X-Y plane, including an inner cylinder portion 25 having a radius of $r_1$, and an outer shell portion 27 having a radius of $r_2$. The X-axis portion of $r_2$ (i.e., r') varies as a function of Z-axis position. The X-axis portion r' extends from the outer surface of the inner cylinder portion 25 to the outer surface of the outer shell portion 27 and can be expressed as a function of Z and $r_2$: $r' = \sqrt{r_2^2 - z^2}$, which is derived from a circle equation ($x^2 + z^2 = r^2$; or in terms of the current variables: $r'^2 + z^2 = r_2^2$). At its maximum, $r' = r_2$ equals one-half the chamber height 20. In terms of distance along the X-axis, the distance from the center of the inner cylinder portion 25 to the outer surface of the outer shell portion 27 at a given Z-axis position can be described as "r", where "r" is:

$$r = r_1 + \sqrt{r_2^2 - z^2} \quad \text{Eqn. 2}$$

The volume of the partially compressed sphere ($Vol_{RBC}$) can then be determined by integrating the area over the Z-axis:

$$Vol_{RBC} = \int_{-r_2}^{r_2} \pi \left(r_1 + \sqrt{r_2^2 - z^2}\right)^2 dz \quad \text{Eqn. 3}$$

$$Vol_{RBC} = \pi \left(\frac{4r_2^3}{3} + 2r_1^2 r_2 + \pi r_1 r_2^2\right) \quad \text{Eqn. 4}$$

According to an aspect of the present invention, therefore, a methodology is utilized wherein (e.g., a processor is adapted such that) a geometric model is assumed for partially compressed spherical RBCs in contact with the interior surfaces of the chamber.

In most instances, the perimeter of an optical density imaged RBC appears somewhat "fuzzy" because the "thickness" of the RBC (e.g., the distance along the Z-axis; and therefore the amount of hemoglobin) decreases near the edge of the RBC. In some instances, the perimeter of an imaged RBC can be further obscured due to factors such as the influence of other RBCs in close proximity, and background fluctuations. In fact, in most analyses of a quiescent sample of substantially undiluted whole blood (1 μl of which typically contains about $4.5 \times 10^6$ RBCs), a substantial number of the RBCs within the analysis chamber are in close proximity to one another. The image shown in FIG. 5, which shows RBCs 22 subjected to an isovolumetric sphering agent, illustrates a typical image of a sample of quiescent substantially undiluted whole blood disposed within a chamber, clearly showing many of the RBCs 22 in close proximity to one another.

Figure 5:
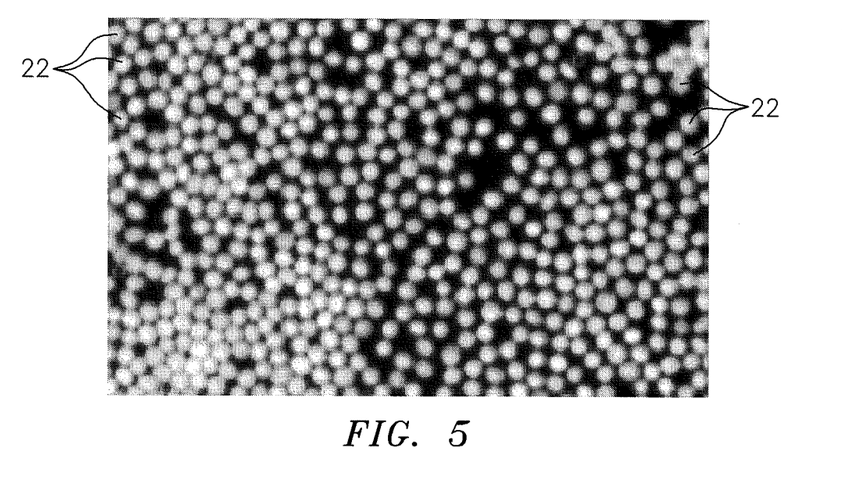
FIG. 5 is an image of isovolumetrically sphered RBCs disposed within a sample.
Figure 6A:
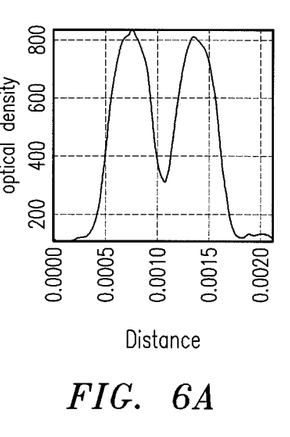
FIG. 6A is an optical density versus distance plot of the image of RBCs shown in FIG. 6B.
Figure 6B:
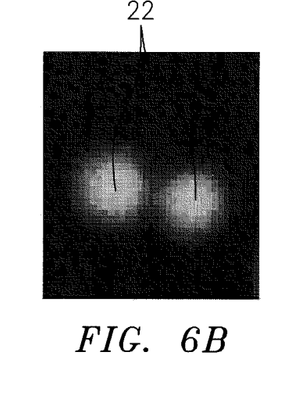
FIG. 6B is an image of a pair of isovolumetrically sphered RBCs disposed within a sample.

The plot of optical density versus distance shown in FIG. 6A, for example, is based on the image of the two RBCs 22 shown in FIG. 6B. The plot and image show two RBCs that are sufficiently separated from one another and that were imaged with low background noise. As a result, each RBC 22 is easily distinguished from the other and the size characteristics of each are ascertainable. The plot shown in FIG. 7A (based on the image shown in FIG. 7B), in contrast, shows that the optical density in the region between the RBCs 22 is less distinctly attributable to either RBC 22. This optical density "blurring" is likely a result of the fact that the RBCs 22 are slightly closer together. The plot shown in FIG. 8A (based on the image in FIG. 8B) illustrates an example where the optical density in the region between the RBCs 22 is even less distinctly attributable to either RBC 22. In those instances where the outer perimeter of an RBC 22 is not readily determinable from an image of the RBC, it is difficult to accurately determine the volume (and/or other evaluative parameters) of that particular RBC due to the interference. Perimeter "blurring" can be addressed by evaluating only those RBCs that are sufficiently separated from other RBCs (i.e., "stand-alone" RBCs). The typical distribution of RBCs in an undiluted sample (see FIG. 5), however, makes it difficult to evaluate only stand-alone RBCs. The present invention provides techniques for addressing RBCs in close proximity to one another.

Figure 7A:
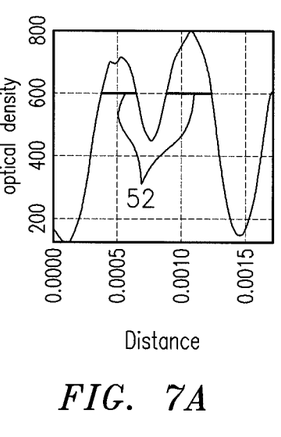
FIG. 7A is an optical density versus distance plot of the image of RBCs shown in FIG. 7B.
Figure 7B:
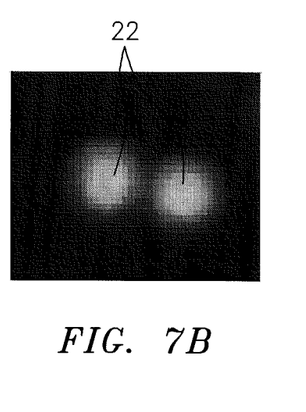
FIG. 7B is an image of a pair of isovolumetrically sphered RBCs disposed within a sample.
Figure 8A:
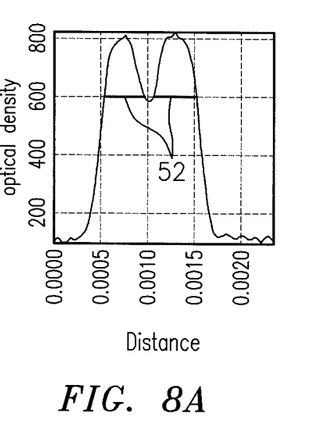
FIG. 8A is an optical density versus distance plot of the image of RBCs shown in FIG. 8B.
Figure 8B:
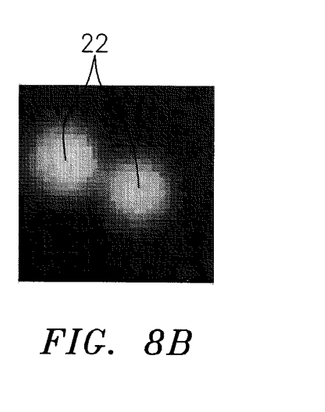
FIG. 8B is an image of a pair of isovolumetrically sphered RBCs disposed within a sample.

According to an aspect of the present invention, RBCs in close proximity to one another may be evaluated by segmentation techniques (or other filtering techniques) wherein only those pixels having an optical density value at or above a certain threshold (or the highest x % of optical density pixels) are provided within the image Limiting the image to those pixels at or above the optical density value threshold will decrease the size of the optical density image of the RBC and eliminate (or minimize, depending on the particular OD value used) the peripheral regions of the RBC that would likely be influenced by adjacent RBCs. Using the optical density graphs shown in FIGS. 6A-8A as an example, an optical density threshold value of about 600 units (e.g., the top 25% of the peak optical density) enables both RBCs in the images to be distinguished from one another. The optical density threshold value that enables sufficiently accurate RBC volume determinations can be arbitrarily chosen for the application at hand and the present invention is not limited to any particular value. The actual volume of a RBC can subsequently be determined as a function of the amount of area covered by the pixels at or above the optical density threshold.

The relationship between the area covered by the pixels at or above the optical density threshold (i.e., the "threshold image") and the actual volume of the RBC can be expressed in several different forms. For example, as described above, a geometrical model can be assigned to the RBC and the difference in volume between a threshold image of an RBC and its actual volume can be determined based on an assumed geometrical model; e.g., the radius of the threshold image may be assumed to be $r=r_1+\alpha r_2$, where "$\alpha$" is a known percentage value between zero and one associated with the size of the threshold image. The actual volume of the RBC is determined using $r=r_1+r_2$, which can then be used in Eqns. 2-4. Alternatively, the relationship between the area covered by the pixels at or above the threshold value and the actual volume of the RBC can be based on clinically significant empirical data (e.g., in table form) that provides a high degree of reliability; e.g., a table relating RBC threshold optical density radius values to statistically accurate actually mean RBC volume values.

Within an image of a sample such as that shown in FIG. 5, there is a range of separation distances between adjacent RBCs; e.g., the inter-RBC spacing is random. As indicated above, the optical density values of the pixels associated with a particular RBC are influenced by adjacent RBCs, and the amount of that influence is a function of the separation distance between the particular RBC and the adjacent RBCs. For accuracy purposes and for increased uniformity, it is useful to analyze RBCs that are similarly situated relative to surrounding RBCs. One technique for selecting similarly situated RBCs involves selecting an area surrounding an RBC and evaluating the optical density values on a per pixel basis within that area. The number of pixels having an optical density value at or above a particular threshold value divided by the total number of pixels within the area can be used as a measure of the density of RBCs surrounding the RBC of interest; i.e., a "threshold density value":

$$\text{Threshold\_density\_value} = \frac{\text{\#\_of\_Pixels\_with\_OD\_value} \geq \_\text{threshold}}{\text{Total\_\#\_of\_Pixels\_in\_Area}}$$

Those analyses that utilize mean values (e.g., MCV, MCHC, MCH, etc.) can be performed on a statistically significant number of RBCs disposed in areas having threshold density values within an acceptable range; e.g., similarly situated RBCs. The above-described methodology for selected similarly situated RBCs is an example of an acceptable methodology, and the present invention is not limited thereto. Once the similarly situated RBCs are chosen, the analyses for the desired parameter (e.g., CV, CHC, etc.) can be performed on each RBC chosen.

The accuracy of the measured area of an RBC can also be affected by the lens system of the analysis device. Some lens systems convolve a point spread function ("PSF") with the RBC profile. In such systems, the resulting image can be blurred and artificially enlarged. To correct the error associated with point spread function, the PSF can be de-convoluted and the image sharpened. Alternatively, the area at a given Z-axis height of an object with a known geometry can be determined from an optical density image. The determined area can then be compared to the known area of the object at the same Z-axis height, and the values compared to calibrate the analysis device. For example, the area of a spherical bead of known diameter can be measured at a particular height within the chamber from the image. The measured area can then be compared to the known area of the bead at the Z-axis height to evaluate the accuracy of the measured area. If necessary, the apparatus can be calibrated to decrease the difference between the measured and theoretical areas and thereby increase the accuracy of the area (and volume) determination.

To determine the mean cell volume (MCV) of the RBCs in the sample, the process described above is repeated for a statistically significant number of the RBCs within the RBC population of the sample. A MCV is statistically determined from the individual RBC data collected. In some embodiments, the accuracy of the MCV determination can be enhanced by basing the determination on cell volume data determined from RBCs that meet predefined criteria relating to the proximity of neighboring RBCs, background noise, etc; i.e., RBCs that are subject to less noise. If the sample contains a sufficient number of RBCs that meet the criteria, then the remaining RBCs (i.e., those which would be problematic to individually determine the cell volume for the reasons stated) can be identified and the MCV can be assigned to those RBCs.

Although this invention has been shown and described with respect to the detailed embodiments thereof, it will be understood by those skilled in the art that various changes in form and detail may be made without departing from the spirit and scope of the invention.

What is claimed is:

1. A method for determining a cell volume of a red blood cell within a blood sample, comprising the steps of:
    depositing the sample into an analysis chamber, the chamber defined by an interior surface of a first panel and an interior surface of a second panel, wherein both panels are transparent, and the chamber has a known or determinable height extending between the interior surfaces of the panels, which height is such that at least one red blood cell subject to an isovolumetric sphering agent assumes a partially compressed spherical shape in contact with the interior surfaces;
    providing an analysis device having an imaging unit and a programmable analyzer;
    imaging the at least one partially compressed spherical red blood cell contacting the interior surfaces using the imaging unit, and producing image signals, wherein the sample quiescently resides within the analysis chamber during imaging;
    using the programmable analyzer to determine a radius r of the partially compressed spherical red blood cell contacting the interior surfaces from the image signals;
    wherein the determined radius r of the partially compressed spherical red blood cell is algorithmically a function of a first portion $r_1$ that extends between a center of an inner cylinder portion of the partiallpressed spherical red blood cell and an outer limit of the inner cylinder portion, and a second portion $r_2$ that extends between the outer limit of the inner cylinder portion and an outer shell portion of the partially compressed spherical red blood cell, which outer shell portion is not in contact with the interior surfaces; and
    using the programmable analyzer to determine a volume of the imaged red blood cell using the determined radius.

2. The method of claim 1, wherein the image signals reflect an optical density image of the partially compressed spherical red blood cell.

3. The method of claim 2, wherein the optical density image is formed from image units, each having an optical density value equal to or greater than a predetermined threshold.

4. The method of claim 3, wherein each image unit is a pixel.

5. The method of claim 4, wherein the determined radius of the partially compressed spherical red blood cell is based on pixels having an optical density value equal to or greater than the predetermined threshold.

6. The method of claim 5, wherein the step of determining the volume of the imaged red blood cell includes determining the volume of the imaged red blood cell based on the determined radius, and increasing the determined volume to include volume attributable to at least an amount of an outer shell portion of the red blood cell not in contact with the interior surfaces.

7. The method of claim 6, wherein the volume attributable to an amount of the outer shell portion is based on empirical data stored within, or accessible by, the processor.

8. A method for determining a mean cell volume of a red blood cell within a blood sample, comprising the steps of:
    depositing the sample into an analysis chamber, the chamber defined by an interior surface of a first panel and an interior surface of a second panel, wherein both panels are transparent, and the chamber has a known or determinable height extending between the interior surfaces of the panels, which height is such that at least one red blood cell subject to an isovolumetric sphering agent assumes a partially compressed spherical shape in contact with the interior surfaces;
    providing an analysis device having an imaging unit and a programmable analyzer;
    imaging a plurality of partially compressed spherical red blood cells within the sample using the imaging unit, which red blood cells are contacting the interior surfaces, and producing image signals reflecting the optical density of the red blood cells contacting the interior surfaces, wherein the sample quiescently resides within the analysis chamber during imaging;
    using the programmable analyzer to determine a threshold density value for a predetermined area surrounding each of a number of the imaged red blood cells, and selecting at least some of the imaged red bloods cells having substantially similar threshold density values;
    using the programmable analyzer to determine a radius r of each of the selected red blood cells having substantially similar threshold density values from the image signals;
    wherein the determined radius r of the partially compressed spherical red blood cell is algorithmically a function of a first portion $r_1$ that extends between a center of an inner cylinder portion of the partially compressed spherical red blood cell and an outer limit of the inner cylinder portion, and a second portion $r_2$ that extends between the outer limit of the inner cylinder portion and an outer shell portion of the partially compressed spherical red blood cell, which outer shell portion is not in contact with the interior surfaces;
    using the programmable analyzer to determine a volume of each of the selected red blood cells using its respective determined radius; and
    using the programmable analyzer to determine a mean red blood cell volume using the determined volumes of the selected red blood cells.

9. The method of claim 8, wherein the radius of each selected red blood cell is determined using image units of the optical density image, which image units each have an optical density value equal to or greater than a predetermined threshold.

10. The method of claim 9, wherein the step of determining the volume of each selected red blood cell includes determining the volume of the selected red blood cell based on the determined radius of the same cell, and increasing the determined volume to include volume attributable to at least an amount of an outer shell portion of the same red blood cell not in contact with the interior surfaces.

11. The method of claim 10, wherein the volume attributable to an amount of the outer shell portion is based on a predetermined geometrical model.

12. The method of claim 11, wherein the volume attributable to an amount of the outer shell portion is based on empirical data stored within, or accessible by the processor.

13. An apparatus for determining a cell volume of at least one red blood cell within a substantially undiluted blood sample, comprising:
- an analysis chamber configured to quiescently hold the sample for analysis, the chamber defined by an interior surface of a first panel, and an interior surface of a second panel, wherein both panels are transparent, and the chamber has a known or determinable height extending between the interior surfaces of the panels, which height is such that at least one red blood cell within the sample will assume a partially compressed spherical shape;
- an imaging unit that includes an illuminator and an image dissector, which unit is operable to image the at least one red blood cell contacting the interior surfaces, and produce image signals representative of such imaged red blood cell; and
- a programmable analyzer adapted to determine, using the image signals, a radius r of the partially compressed spherical red blood cell contacting the interior surfaces from the image signals, and a volume of the imaged red blood cell using the determined radius;
- wherein the determined radius r of the partially compressed spherical red blood cell is algorithmically a function of a first portion $r_1$ that extends between a center of an inner cylinder portion of the partially compressed spherical red blood cell and an outer limit of the inner cylinder portion, and a second portion $r_2$ that extends between the outer limit of the inner cylinder portion and an outer shell portion of the partially compressed spherical red blood cell, which outer shell portion is not in contact with the interior surfaces.

* * * * *